United States Patent [19]

Dubler et al.

[11] Patent Number: 5,073,629

[45] Date of Patent: Dec. 17, 1991

[54] METHADONE FLUORESCENCE POLARIZATION IMMUNOASSAY

[75] Inventors: Robert E. Dubler, Gurnee; Susan A. Thacker, Naperville; John A. Walling, Round Lake Beach; Nai-Yi Wang, Mundelein, all of Ill.

[73] Assignee: Abbott Laboratories, Abbott Park, Ill.

[21] Appl. No.: 300,670

[22] Filed: Jan. 23, 1989

[51] Int. Cl.$^5$ .................... C07K 17/02; C07K 15/14; G01N 33/536

[52] U.S. Cl. .................... 530/405; 530/345; 530/363; 530/380; 530/386; 530/395; 530/403; 530/404; 530/406; 530/408; 530/409; 436/536; 436/546

[58] Field of Search ............... 530/345, 363, 386, 395, 530/380, 403, 404, 405, 406, 409, 408; 436/546, 536

[56] References Cited

U.S. PATENT DOCUMENTS

| | | | |
|---|---|---|---|
| 3,704,282 | 11/1972 | Spector | 530/345 |
| 3,817,837 | 6/1974 | Rubenstein et al. | 435/79 |
| 3,843,696 | 10/1974 | Wagner et al. | 260/404 |
| 3,940,475 | 2/1976 | Gross | 436/500 |
| 3,966,556 | 6/1976 | Rubenstein et al. | 435/188 |
| 3,996,344 | 12/1976 | Gross | 436/537 |
| 4,016,146 | 4/1977 | Soares | 530/405 |
| 4,022,878 | 5/1977 | Gross | 436/500 |
| 4,041,076 | 8/1977 | Avenia et al. | 564/114 |
| 4,097,586 | 6/1978 | Gross | 436/500 |
| 4,104,367 | 8/1978 | Gomez et al. | 436/542 |
| 4,122,078 | 10/1978 | Yoshioka et al. | 530/363 |
| 4,255,329 | 3/1981 | Ullman | 540/589 |
| 4,329,281 | 5/1982 | Christenson et al. | 530/363 |
| 4,351,760 | 9/1982 | Khanna et al. | 530/395 |
| 4,420,568 | 12/1983 | Wang et al. | 436/536 |
| 4,476,228 | 10/1984 | Huckzermeier et al. | 436/500 |
| 4,476,229 | 10/1984 | Fino et al. | 436/500 |
| 4,481,136 | 11/1984 | Khanna et al. | 530/391 |
| 4,492,762 | 1/1985 | Wang et al. | 436/537 |
| 4,510,251 | 4/1985 | Kirkemo et al. | 436/536 |
| 4,585,862 | 4/1986 | Wang et al. | 544/319 |
| 4,588,697 | 5/1986 | Khanna et al. | 436/518 |
| 4,593,089 | 6/1986 | Wang et al. | 536/13.6 |
| 4,681,859 | 7/1987 | Kramer | 436/501 |
| 4,751,190 | 6/1988 | Chiapetta et al. | 436/546 |

FOREIGN PATENT DOCUMENTS

| | | |
|---|---|---|
| 0199042 | 10/1986 | European Pat. Off. |
| 0201751 | 11/1986 | European Pat. Off. |
| 0218010 | 4/1987 | European Pat. Off. |
| 0240021 | 10/1987 | European Pat. Off. |
| 56-125666 | 10/1981 | Japan. |
| 2111476A | 7/1983 | United Kingdom. |

OTHER PUBLICATIONS

Shipchandler, M. T. et al., "4'-[Aminomethyl]fluorescein and Its N-Alkyl Derivatives: Useful Reagents in Immunodiagnostic Techniques", Analytical Biochemistry, 162:89–101 (1987).

Liu, Chi-Tan et al., "Immunologic Studies on Drug Addiction", The Journal of Immunology, 111:2, 472–477, Aug. 1973.

Riceberg, Louis J. et al., "Estimation of $\beta$-3,4-Dimethoxyphenethylamine and Related Compounds in Urine Extracts by Radioimmunoassay", Chemical Pharmacology, 24:259–265, 1975.

McGilliard, K. L. et al., "Stereospecific Radioimmunoassay of d- and l-Methadone", Proc. West. Pharmacol. Soc., 22:463–466 (1979).

Bartos, Frantisek et al., "Stereospecific Antibodies in Methadone", Research Communications in Chemical Pathology and Pharmacology, 16:1, 131–143, Jan. 1977.

Manning, Thomas et al., "Evaluations of the Abuscreen for Methadone", Journal of Forensic Sciences, 267:112–120 (1975).

Syva Company, "Emit d.a.u. Methadone Assay", Nov. 1987.

Primary Examiner—Jeffrey E. Russel
Assistant Examiner—Kay Kim
Attorney, Agent, or Firm—James D. McNeil; Roberta Hastreiter; Thomas M. Breininger

[57] ABSTRACT

A fluorescence polarization immunoassay for detecting the presence of methadone in a test sample is provided, based upon competition between methadone and a fluorescently labeled tracer for the binding sites on an antibody specific for methadone. The concentration of methadone in the sample determines the amount of tracer that binds to the antibody. The amount of tracer-antibody complex formed can be quantitatively measured and is inversely proportional to the quantity of methadone in the sample. Tracers used as reagents and immunogens used to raise antibodies for use as reagents are also disclosed.

6 Claims, No Drawings

METHADONE FLUORESCENCE POLARIZATION IMMUNOASSAY

BACKGROUND OF THE INVENTION

1. Field of the Invention

This invention relates to a method and reagents for detecting methadone in a test sample such as urine. In particular, the invention relates to a fluorescence polarization immunoassay procedure for determining the presence or amount of methadone in a sample, tracer compounds used as reagents in such procedure, and immunogen compounds used to raise antibodies for use as reagents in such procedure.

2. Description of Related Art

Methadone is a synthetic narcotic analgesic which has been used in maintenance programs as a treatment for morphine and heroin addiction. Methadone staves off the acute effects of withdrawal from heroin, and also reduces or eliminates the postaddiction syndrome of anxiety, depression, and craving. Excessive use of this drug, however, may lead to habituation or addiction.

The biological fluid used most frequently for detecting methadone is urine. Other biological samples, however, such as serum, plasma or tissue can be used as test samples. In the past, methadone has been detected by a number of techniques including thin-layer chromatography (TLC), gas chromatography (GC) and high performance liquid chromatography (HPLC). These methods generally involve complicated chemical extractions of the drugs from the test sample, procedures which require highly trained personnel and lengthy assay times.

Binding assays have provided a preferable alternative to chemical methods such as GC, TLC and HPLC. Binding assays for detecting antigens and antibodies depend upon the immunological reactivity which characterizes these substances. Generally, these assays are collectively termed immunoassays.

Immunoassay techniques take advantage of the mechanisms of the immune systems of higher organisms, wherein antibodies are produced in response to the presence of antigens which are foreign to the organisms. One or more antibodies are produced in response to, and are capable of reacting with, a particular antigen, thereby creating a highly specific reaction mechanism which can be used in vitro to determine the presence or concentration of that particular antigen in a biological sample.

Competitive binding assays for measuring analytes of interest are based on the competition between the analyte in the test sample and a labeled reagent (i.e., tracer) for a limited number of binding sites on a binding member (e.g., and antibody) that is specific for both the analyte and tracer. The concentration of analyte the sample determines the amount of tracer that will bind to the antibody. The amount of tracer-antibody complex formed can be quantitatively measured and is proportional to the quantity of analyte in the test sample.

Fluorescence polarization techniques provide a quantitative means for measuring the amount of tracer-antibody complex formed in a competitive binding immunoassay. These techniques are based on the principle that a fluorescently labeled tracer rotates rapidly when excited by linearly polarized light, and fluorescent light emitted by the rotating tracer becomes partially depolarized due to the rapid rotation. As a result, the tracer will emit fluorescence with a degree of polarization inversely related to the tracer's rate of rotation, i.e., the higher the rotation the lower the polarization of the emitted light (or the greater the depolarization of the emitted light). The speed of rotation and the amount of depolarization decrease when the tracer becomes bound to a heavier molecule, such as when it becomes bound to the comparatively heavier antibody molecule. If a fluorescent tracer-antibody complex is excited by linearly polarized light, more of the emitted light remains polarized because the fluorophore is constrained from rapidly rotating. When a "free" tracer (i.e., tracer that is not bound to an antibody) is excited by linearly polarized light, its rotation is much faster than that of the complex, and therefore, the emitted light is depolarized.

The fluorescence polarization immunoassay (FPIA) is a homogenous assay wherein the final polarization readings are taken from a solution in which bound tracer is not separated from free tracer. In heterogeneous immunoassay procedures, the bound tracer must be separated from the free tracer before a reading can be taken.

By using standard preparations for comparsion with a test sample containing an unknown level of the analyte, the FPIA provides a quantitative means for measuring the amount of tracer-antibody complex formed in a competitive binding assay. This procedure is currently being employed by Abbott Laboratories in its commercially available TDx ® Therapeutic Drug Monitoring System and is described in U.S. Pat. No. 4,269,511 and U.S. Pat. No. 4,420,568.

As disclosed in the '511 and '568 patents, because the tracer must compete with the analyte for binding to the antibody in a FPIA, the tracer must possess a molecular structure sufficiently similar to the analyte to enable the tracer to be recognized by an antibody specific for the analyte. For this reason, the tracer is also referred to as a fluorescently labeled analyte-analog, a substantial portion of which has the same spatial and polar organization as the analyte to define one or more determinants capable of competing with the analyte for the binding sites on the antibody.

A need exists for providing an assay and reagents for performing an accurate and sensitive FPIA for the detection of the presence of methadone in a sample.

SUMMARY OF THE INVENTION

The present invention provides a method for detecting the presence or amount of methadone in a test sample using fluorescence polarization techniques. The method comprises the steps of:

a) contacting the sample with a fluorescently labeled tracer and an antibody capable of specifically recognizing methadone and the tracer to obtain a solution;
b) passing plane-polarized light through the solution to obtain a fluorescence polarization response; and
c) detecting the fluorescence polarization response as a measure of the presence or amount of methadone in the sample.

The present invention further provides tracer compounds used as reagents in such method, and immunogen compounds used to raise antibodies for use as reagents in such method.

DETAILED DESCRIPTION OF THE INVENTION

The present invention provides reagents and a method for the detection of methadone in a sample.

DEFINITIONS

The following definitions are applicable to the present invention:

The term "determinants", as used herein, refers to those regions of the antigen which are involved in specific binding reactions between antigens and antibodies. In essence, it is the determinants which differentiate antigens, and therefore, antibodies from one another on the basis of immunological specificity.

The term "analyte", as used herein, refers to a molecule to which a binding member such as an antibody can be obtained or formed. The analyte of interest in the present invention is methadone which has the following structure:

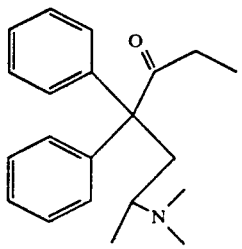

Such an analyte is a protein-free compound, of low molecular weight, generally in the range of 50 to 4000, more preferably in range of 100 to 2000. Such an analyte does not induce antibody formation when injected into an animal but is reactive to antibodies.

The term "analyte-analog", as used herein, refers to a molecule which has substantially the same spatial and polar organization as one or more determinants of the analyte of interest. Such an analyte-analog is a protein-free compound, of low molecular weight, generally in the range of 50 to 4000, more preferably in the range of 100 to 2000. This duplication of the determinant(s) enables the analyte-analog to compete with the analyte in the test sample for a binding site on an analyte-specific binding member, such as an antibody. In addition, the analyte-analog can be modified such that it is not identical to the analyte while retaining the necessary determinant(s) for binding to an analyte-specific binding member.

The structure of the analyte-analog determinant(s) need not be identical to that of the analyte; it is sufficient that the analyte-analog substantially duplicate the appropriate determinant(s). Therefore, the analyte-analog can be any molecular structure which contains chemical groups, amino acids, or nucleotides different from those of the analyte, so long as that analyte-analog substantially duplicates the analyte determinant(s) such that a specific binding member (i.e., antibody, receptor, nucleotide sequence, etc.) will recognize and bind to that substantially duplicated determinant(s).

The term "analyte-specific binding member", as used herein, refers to a member, such as an antibody or receptor, that specifically binds to the analyte. Antibodies to such an analyte are typically raised by first conjugating the analyte or analyte-analog to a protein carrier and injecting the conjugate into an animal. The resulting antibodies can be isolated by conventional, well-known antibody isolation techniques.

The term "tracer", as used herein, refers to an analyte or analyte-analog which is attached to a fluorescent molecule, described hereinafter. The fluorescent molecule is the detectable component of the tracer.

In accordance with the method of the present invention, a test sample suspected of containing an analyte of interest is mixed with a tracer and an antibody specific for the analyte and the tracer. Any analyte present in the sample and the tracer compete for a limited number of binding sites on the antibody, resulting in the formation of analyte-antibody and tracer-antibody complexes. By maintaining constant the concentration of tracer and antibody, the ratio of the formation of analyte-antibody complex to tracer-antibody complex is directly proportional to the amount of analyte present in the sample.

The amount of analyte in the sample is determined by exciting the mixture with polarized light and measuring the polarization of the fluorescence emitted by free tracer and tracer-antibody complex. A tracer which is not complexed to an antibody is free to rotate in less than the time required for absorption and re-emission of fluorescent light. As a result, the re-emitted light is relatively randomly orientated so that the fluorescence polarization of a tracer not complexed to an antibody is low, approaching zero. Upon complexing with a specific antibody, the tracer-antibody complex thus formed assumes the rotation of the antibody molecule, which is slower than that of the relatively small tracer molecule, thereby increasing the polarization observed. Therefore, when an analyte competes with the tracer for antibody sites, the observed polarization of fluorescence of the tracer-antibody complex becomes a value somewhere between that of the free tracer and the tracer-antibody complex. If the sample contains a high concentration of the analyte, the observed polarization value is closer to that of the free tracer, i.e., low. If the sample contains a low concentration of the analyte, the polarization value is closer to that of the bound tracer, i.e., high. By sequentially exciting the reaction mixture of an immunoassay with vertically and then horizontally polarized light, and analyzing only the vertical component of the emitted light, the polarization of the fluorescence in the reaction mixture can be accurately determined. The precise relationship between polarization and concentration of the analyte to be determined is established by measuring the polarization values of calibrators having known concentrations. The concentration of the analyte can be interpolated from a standard curve prepared in this manner.

The immunoassay according to the invention is referred to as a homogenous assay, which means that the final polarization readings are taken from a solution in which bound tracer is not separated from free tracer. This is a distinct advantage over heterogeneous immunoassay procedures, wherein the bound tracer must be separated from the free tracer before a reading can be taken.

The choice of the fluorescent molecule for labeling the analyte-analog and thereby forming the tracer is advantageously flexible and is largely up to the preferences of the practitioner. It will be readily appreciated that the fluorescent labels are ideally chosen in accordance with their size, that is, the smaller the molecule, the more rapid it can rotate, an d the more effective it is as an FPIA tracer component. In the present invention, the preferred fluorescent labels are fluorescein and fluorescein derivatives. These compounds provide fluorescent response when excited by polarized light of an appropriate wavelength and thereby enable the fluorescence polarization measurement. For example, any of the following fluorescein derivatives can be used: fluorescein amine; carboxyfluorescein; alphaiodoacetamidofluorescein; aminomethylfluorescein; N-alkyl aminomethylfluorescein: 2,4-dichloro-1,3,5-triazin-2-yl-amino fluorescein (DTAF); 4-chlor-6-methoxy-1,3,5-triazin-2-yl-amino fluorescein; and fluorescein isothiocyanate. Especially preferred fluorescein derivatives are aminomethylfluorescein and fluorescein amine (isomers I and II).

Fluorescein exists in two tautomeric forms depending on the acid concentration (pH) of the environment. In the open (acid) form, fluorescein or a fluorescein derivative (or a tracer containing a fluorescent molecule) is capable of absorbing blue light and emitting green fluorescence after an excited state lifetime of about four nanoseconds. When the open and closed forms coexist, the relative concentration of molecules in the open and closed forms is easily altered by adjustment of the pH level. Generally, the tracers of the present invention are prepared in solution as biologically acceptable salts such as sodium, potassium, ammonium and the like, which allows the compounds to exist in the open, fluorescent form. The specific salt present will depend on the buffer used to adjust the pH level. For example, in the presence of sodium phosphate buffer, the compounds of the present invention will generally exist in the ope form, as a sodium salt.

As used herein, the term "fluorescein", either as an individual compound or as a component of a tracer, is meant to include both the open and closed forms, if they exist for a particular molecule, except in the context of fluorescence. An open form is necessary for the fluorescence to occur.

The particular tracers formed in accordance with this invention have been found to produce good assay results, as will be demonstrated in the Examples. The concentration of the analyte which can be determined in accordance with the present invention is from about $10^{-6}$ to about $10^{-10}$M. Higher concentrations of analyte can be determined by diluting the test sample. Although the concentration range of analyte in the sample will determine the range of concentration of the test reagents, i.e., tracer and antibody, the individual reagent concentrations are determined empirically to optimize the sensitivity of the assay. Suitable concentrations of the tracer and antibody can be ascertained by one of ordinary skill in the art.

REAGENTS

1. Haptens

Haptens which are structurally similar to methadone are prepared for use as immunogens to raise antibodies, and/or analyte-analogs of tracers. The poly(amino acid) carrier or fluorescent molecule is attached to the hapten by functionalizing the ethyl ketone sidechain of methadone, or replacing the dimethylamino sidechain of methadone with a spacer group.

A preferred hapten of the present invention is represented by the following structure:

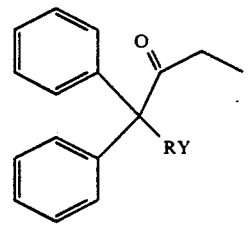

wherein:
R is a spacer group consisting of from 0 to 15 carbon atoms and heteroatoms, including not more than six heteroatoms, arranged in a straight or branched chain, saturated or unsaturated, with the proviso that not more than two heteroatoms may be linked in sequence and that branchings may occur only on carbon atoms; and
Y is a linking group selected from —COOH, —NH$_2$, —CHO, and —OH.

When R involves only carbon atoms, it is preferred that R is from 1 to 10 carbon atoms. Suitable heteroatoms include nitrogen, oxygen, sulfur, silicon and phosphorus. For example, where R includes nitrogen and oxygen as heteroatoms, R can be —CH$_2$CH=N—O—CH$_2$—. It appears that compounds with more than two heteroatoms linked in sequence are less stable.

Another preferred hapten of the present invention is represented by the following structure:

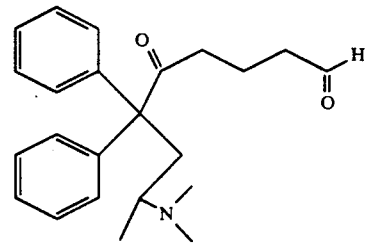

The haptens are prepared according to methods known to those skilled in the art to produce compounds with a sidechain containing chemical groups substantially similar to those of the desired determinant(s). These compounds, or their derivatives, are then attached to either a poly(amino acid) carrier or fluorescent molecule.

In a FPIA, the tracer and any methadone present in the test sample compete for the binding sites on the antibody. Many variations in the structure of the immunogens and tracers are allowed in achieving this goal.

2. Antibodies

The antibodies utilized in the present invention are prepared by developing a response in an animal to one of the immunogens described hereinafter. The immunogen is administered and the appropriate antibodies are selected according to methods well-known to those skilled in the art. Although rabbits and sheep were the immune hosts used in the experiments described herein, any in vivo or in vitro host capable of producing antibodies to the immunogens can be used. The antibodies bind with any methadone present in the test sample as well as with the tracer.

a. Structure of Immunogens

Immunogens can be produced from a wide variety of methadone derivatives. The immunogens of the present invention have one of the following general structures:

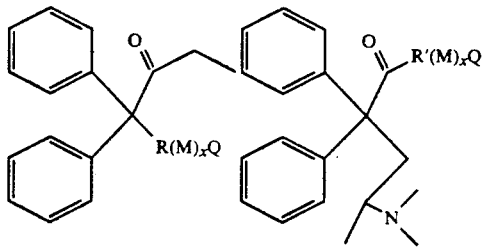

wherein:
R is a spacer group consisting of from 0 to 15 carbon atoms and heteroatoms, including not more than six heteroatoms, arranged in a straight or branched chain, saturated or unsaturated, with the proviso that not more than two heteroatoms may be linked in sequence and that branchings may occur only on carbon atoms;

R' is a spacer group consisting of from 0 to 15 carbon atoms and heteroatoms, including not more than six heteroatoms, arranged in a straight or branched chain, saturated or unsaturated, with the proviso that not more than two heteroatoms may be linked in sequence;

x is 0 or 1;

M is a linking group selected from C=O, —NH—, O—C=O, N—C=O, and N—C=S; and

Q is an immunogenic carrier.

Analogous to the haptens as described above, when R or R' involves only carbon atoms, it is preferred that R or R' is from 2 to 10 carbon atoms. The same heteroatoms, as described previously, can be utilized. In some instances, there is no linking group M present.

An immunogen which elicited a good antibody response according to the tests carried out has the following structure:

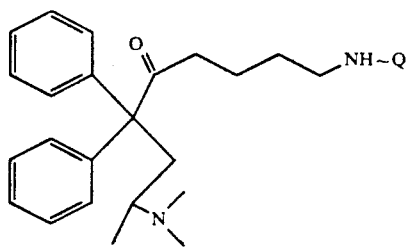

wherein:
Q is a poly(amino acid) immunogenic carrier.

A variety of protein carriers can be used as the poly(amino acid) immunogenic carrier. Suitable immunogenic carriers include albumins, serum proteins (e.g., globulins), ocular lens proteins, lipoproteins and the like. Illustrative protein carriers are bovine serum albumin (BSA), keyhole limpet hemocyanin, egg ovalbumin, thyroglobulin and bovine gamma-globulin. Thyroglobulin is a preferred immunogenic carrier. Alternatively, synthetic poly(amino acids) having a sufficient number of available amino groups, such as those in the amino acid lysine, can be utilized.

b. Synthesis of Immunogens

In the immunogens of the present invention, the chemical bonds between the carboxyl group-containing methadone haptens and the amino groups on a protein carrier can be established using a variety of methods known to those skilled in the art. It is frequently preferable to form amide bonds. Amide bonds are formed by first activating the carboxylic acid moiety of the methadone hapten by reaction with a leaving group reagent (e.g., N-hydroxysuccinimide, 1-hydroxybenztriazole, p-nitrophenol and the like). An activating reagent such as 1,3-dicyclohexylcarbondiimide, diisopropylcarbondiimide and the like can be used. The activated form of the methadone hapten is then reacted with a buffered solution containing the protein carrier. Alternatively, the carboxylic acid hapten may be converted, with or without isolation, into a highly reactive mixed anhydride or mixed carbonate and then combined with the protein carrier.

A methadone hapten with a terminal amine functionality can be transformed into a highly reactive N-hydroxysuccinimide urethane by reaction with N,N'-disuccinimidyl carbonate in a suitable solvent, such as acetonitrile or dimethylformamide. The resultant urethane is then reacted with the protein carrier in a buffered, aqueous solution to provide an immunogen.

A methadone hapten with a terminal aldehyde functionality can be coupled to the protein carrier, in a buffered, aqueous solution and in the presence of sodium cyanoborohydride, by reductive amination according to methods known to those skilled in the art.

Alternatively, a methadone hapten containing an alcohol group can be coupled to the protein carrier by first reacting it with phosgene or a phosgene equivalent, such as diphosgene or carbodiimidizole, resulting in the formation of a highly reactive chloroformate or imidazoloformate derivative (usually without isolation). The resultant active formate ester is then reacted with the protein carrier in a buffered, aqueous solution to provide an immunogen.

3. Tracers a. Structure of Tracers

The tracers of the present invention can be produced from a wide variety of methadone derivatives and have the following structure:

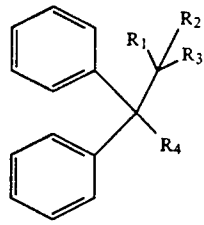

wherein:
$R_1$ and $R_2$ are H or OH, or $R_1$ and $R_2$ together are C=O;

$R_3$ is ethyl or RZFl; and $R_4$ is 2-dimethylaminopropyl when $R_3$ is RZFl, and $R_4$ is RZFl when $R_3$ is ethyl; wherein,
R is a spacer group consisting of from 0 to 15 carbon atoms and heteroatoms, including not more than six heteroatoms, arranged in a straight or branched chain, saturated or unsaturated, with the proviso that not more than two heteroatoms may be linked in sequence and that branchings may occur only on carbon atoms;

Z is a linking group selected from C=O, —NH—, O—C=O, N—C=O, and N—C=S; and

Fl is fluorescein or a fluorescein derivative.

As described above, when R involves only carbon atoms, it is preferred that R is from 2 to 10 carbon atoms. The same heteroatoms as described above can be used. For example, where R includes nitrogen as a heteroatom, R can be —(CH$_2$)$_4$NHCH$_2$CH$_2$—.

A tracer which exhibited good binding has the following structure:

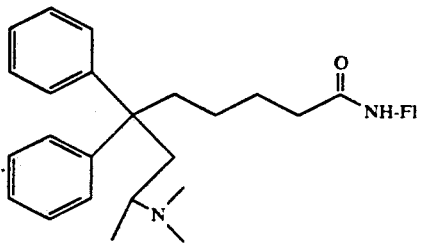

wherein:

Fl is fluorescein or a fluorescein derivative.

b. Synthesis of Tracers

A methadone hapten, prepared as described above, containing either an amino group or a carboxyl group can be coupled to fluorescein or a fluorescein derivative to prepare the tracers of the present invention. A methadone hapten with a terminal carboxyl group can be coupled to an amino-terminal fluorescein derivative by first activating the carboxylic acid moiety with an activating agent such as 1,3-dicyclohexylcarbodiimide, which is then reacted with a leaving group reagent such as N-hydroxysuccinimide, 1-hydroxybenztriazole, p-nitrophenol or the like, to prepare an activated hapten. The activated hapten is then allowed to react with a solution of the fluorescein derivative, resulting in the formation of a tracer. Other activating agents, such as N,N'-disuccinimidyl carbonate and 2-ethyl-5-phenylisoxolium-3'-sulfonate can be used. Alternatively, the carboxylic acid hapten may be converted, with or without isolation, into a highly reactive acyl chloride, mixed anhydride, mixed carbonate or acyl imidazolide and then combined with the amino-terminal fluorescein derivative.

A methadone hapten with a terminal amine functionality can be transformed into a highly reactive N-hydroxysuccinimide urethane by reaction with N,N'-disuccinimidyl carbonate in a suitable solvent, such as acetonitrile or dimethylformamide. An urea coupling to an amino-terminal fluorescein moiety can then be effected by combining the resultant urethane with the fluorescein derivative in a solution of dimethylformamide or other suitable solvent, usually made basic. An amino group-containing hapten can also be coupled to a carboxyfluorescein derivative which has been activated with N-hydroxysuccinimide in a suitable solvent.

Alternatively, a methadone hapten containing an alcohol group can be coupled to an amino-terminal fluorescein derivative by first reacting it with phosgene or a phosgene equivalent, such as diphosgene or carbodiimidizole, resulting in the formation of a highly reactive chloroformate or imidazoloformate derivative (usually without isolation). The resultant active formate ester is then reacted with an amino-terminal fluorescein derivative in a suitable solvent, such as dimethylformamide, resulting in the formation of a tracer.

4. Assay Method

The tracers and antibodies raised against immunogens of the present invention produce excellent results in a fluorescence polarization assay of the present invention for the semi-quantitative detection of methadone.

The assays are performed in accordance with the following general procedure:

1) a measured volume of standard or test sample containing or suspected of containing methadone is delivered into a test tube;
2) a known concentration of tracer is then added to the tube;
3) a known concentration of analyte-specific antibody, produced using the immunogen as described above, is added to the tube;
4) the reaction mixture is incubated, wherein the tracer and analyte compete for limited antibody binding sites, whereby tracer-antibody and analyte-antibody complexes form; and
5) the amount of tracer-antibody complex is measured by fluorescence polarization techniques to determine the presence or amount of analyte in the test sample.

The preferred procedure was designed to be conducted on the TDx ® Therapeutic Drug Monitoring System or the ADx ™ Abused Drug System, both of which are available from Abbott Laboratories, Abbott Park, Ill. When either the TDx or ADx system is used, the assays are fully automated from pre-treatment to final reading. Manual assays, however, can also be performed. Although the principles of the invention are applicable to manual assays, the automated nature of the TDx and ADx systems assures minimal technician time to perform assays and interpret data. The results can be quantified in terms of "millipolarization units", "span" (in millipolarization units) and "relative intensity". The measurement of millipolarization units indicates the maximum polarization when a maximum amount of the tracer is bound to the antibody in the absence of any methadone in the test sample. The higher the net millipolarization units, the better the binding of the tracer to the antibody. For the purposes of the present invention, a net millipolarization value of at least approximately 150 is preferred.

The span is an indication of the difference between the net millipolarization and the minimum amount of tracer bound to the antibody. A larger span provides for a better numerical analysis of data. For the purposes of the present invention, a span of at least approximately 80 millipolarization units is preferred.

The intensity is a measure of the strength of the fluorescence signal above the background fluorescence. Thus, a higher intensity will give a more accurate measurement. The intensity is determined as the sum of the vertically polarized intensity plus twice the horizontally polarized intensity. The intensity can range from a signal of about three times to about thirty times the background noise, depending upon the concentration of the tracer and other assay variables. For the purposes of the present invention, an intensity of about ten to about twenty times that of background noise is preferred.

The pH at which the method of the present invention is practiced must be sufficient to allow the fluorescein moiety of the tracers to exist in their open form. The pH can range from about 4 to 9, preferably from about 6 to 8, and most preferably from about 7.0 to 7.5. Various buffers can be used to achieve and maintain the pH during the assay procedure. Representative buffers include borate, phosphate, carbonate, Tris, barbital and the like. The particular buffer used is not critical to the present invention, but the Tris and phosphate buffers are preferred.

Additionally, riboflavin binding protein (RBP) can be utilized in the assay system to prevent fluorescent interference due to riboflavin. Riboflavin, or vitamin $B_2$, is a common constituent of many foods and commercially available vitamin supplements. Riboflavin is excreted in urine and has a fluorescence spectrum similar to that of fluorescein. Ordinary consumption of riboflavin is unlikely to produce more than trace amounts of riboflavin in urine, however, urine test results can be distorted by the consumption of excessive quantities of riboflavin by persons wishing to prevent the detection of methadone.

EXAMPLES

The following Examples describe methods of immunogen and tracer synthesis as well as assays which were performed in accordance with the present invention.

Synthesis of Immunogens

EXAMPLE 1

2-dimethylamino-4,4-diphenyl-5-oxo-nonanal, thyroglobulin immunogen

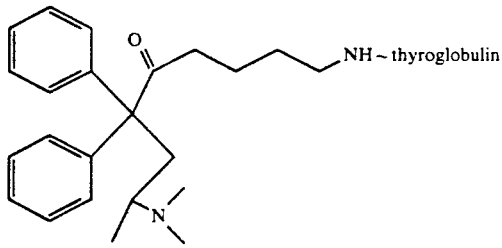

A solution of 2,2 diphenylacetonitrile (55 g) in tetrahydrofuran (THF, 135 ml) was added dropwise to a stirring slurry of sodium hydride (80% in mineral oil, 17.1 g, washed twice with hexane) and anhydrous THF (90 ml), under nitrogen. Stirring was continued until the evolution of gas ceased, approximately 20 min. Solid 2-dimethylaminoisopropyl chloride hydrochloride (45 g) was added, and the resultant mixture was stirred at reflux for 5 hours. Water was added, and the aqueous mixture was extracted with ethyl acetate (3×). The combined extracts were washed with water and brine (once each) and dried (MgSO$_4$). Rotary evaporation of the solution gave a light brown oil which was recrystallized from hexane/ethyl acetate (100:1) to yield 24 g of 4-dimethylamino-2,2-diphenylpentanenitrile as a white solid.

A solution of 1.5M diisobutylaluminum hydride in toluene (7.5 ml) was added to a stirring solution of 4-dimethylamino-2,2-diphenylpentanenitrile (3 g) in THF (7.5 ml), at −78° C. under nitrogen. The resultant mixture was then removed from the dry ice-acetone bath and allowed to warm to room temperature. Stirring was continued at room temperature for 1 day. Saturated ammonium chloride solution was added, and the resultant mixture was extracted with ethyl acetate (3×). The combined extracts were washed with brine and dried (MgSO$_4$). An equal volume of 10% sulfuric acid was added, and the mixture was stirred at room temperature for 3 hours. Water was added, and the aqueous mixture was again extracted with ethyl acetate (3×). The combined extracts were washed with water and dried (MgSO$_4$). Rotary evaporation of the solution gave a crude product which was treated with anhydrous ether. The separated solid material was filtered off, and the filtrate was again rotary-evaporated to yield 1.4 g of 4-dimethylamino-2,2-diphenylpentanal, as a viscous residue which solidified upon standing.

A solution of 5-bromo-1-pentene (4.8 g) in anhydrous THF was added dropwise to magnesium turnings (1 g) in THF (15 ml), under nitrogen with vigorous stirring. After the initial exothermic reaction had subsided, the mixture was stirred at 45° C. for 4 hours. A solution of 4-dimethylamino-2,2-diphenylpentanal (1.2 g), as prepared above, dissolved in THF (5 ml) was then added. The resultant mixture was stirred for 18 hours. Saturated ammonium chloride solution was added and the aqueous mixture was partitioned between water and ethyl acetate (3×). The combined organic layers were washed with brine and water (once each), and dried (MgSO$_4$). Rotary evaporation of the solution gave a crude material which was flash-chromatographed over silica gel. Elution with chloroform (CHCl$_3$)/methanol (20:1) yielded 0.6 g of 2-dimethylamino-4,4-diphenyl-9-decene-5-ol, as a mixture of two isomers.

Anhydrous dimethyl sulfoxide (DMSO, 8.8 ml) was carefully added by syringe to a stirred solution of oxalyl chloride (4.8 ml) in methylene chloride (40 ml), maintained at −50° C. to −60° C. The mixture was then stirred 2 min. A solution of 2-dimethylamino-4,4-diphenyl-9-decene-5-ol (1 g) in methylene chloride (2 ml) was added, and stirring continued for 5 min. The mixture was allowed to warm to room temperature, diluted with water, and washed with sodium bicarbonate solution. Rotary evaporation of the solution gave a crude product which was flash-chromatographed over silica gel. Elution with chloroform/methanol (20:1) yielded 0.5 g of 2-dimethylamino-4,4-diphenyl-9-decene-5-one.

Trifluoroacetic acid (1 ml) was added to a solution of 2-dimethylamino-4,4-diphenyl-9-decene-5-one (270 mg) in methanol (5 ml) to adjust the pH to 2.0. The solution was rotary evaporated, and the residue was taken up in methanol. A gentle stream of ozone was passed through the solution at −78° C., until the color turned to sky blue. The reaction was warmed to −20° C., and dimethyl sulfide (3 ml) was added. Rotary evaporation of the solution gave a crude material which was flash-chromatographed over silica gel. Elution with chloroform/methanol (30:1) yielded 80 mg of 2-dimethylamino-4,4-diphenyl-5-oxo-nonanal.

Eighteen milligrams of 2-dimethylamino-4,4-diphenyl-5-oxo-nonanal (0.051 mmol) was dissolved in DMSO (1.0 ml), swirling to dissolve the hapten off the sides of the scintillation vial. A 10 mg/ml thyroglobulin solution was prepared by dissolving 200 mg of thyroglobulin in 20 ml 0.05M phosphate buffer, pH 9.0. The dissolved hapten was added dropwise to the thyroglobulin solution. The hapten vial was rinsed with an additional 0.5 ml DMSO and added dropwise to the solution. The resultant mixture was stirred at room temperature for 1 hour. Five milligrams of sodium cyanoborohydride was added to the mixture, and the solution was stirred at room temperature for 0.5 hours. The pH of the solution was adjusted to 7.3 with 0.1 N HCl. An additional 5.0 mg sodium cyanoborohydride was added, and the solution was again stirred for 0.5 hours. This was repeated once more, for a total addition of 15.0 mg sodium cyanoborohydride. This solution was dialyzed against 0.05M phosphate buffer, pH 7.5, to produce a solution of 2-dimethylamino-4,4-diphenyl-5-oxo-nonanal, thyroglobulin immunogen.

EXAMPLE 2

3,3-diphenyl-4-oxo-hexanal, thyroglobulin immunogen

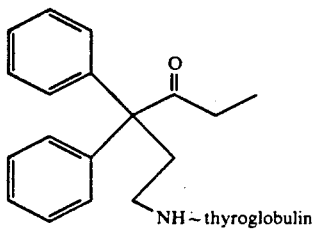

A solution of 2,2-diphenylacetonitrile (9.15 g) in THF (22.5 ml) was added dropwise to a stirred slurry of 80% sodium hydride (2.85 g, washed twice with hexane) and THF, under nitrogen. The mixture was stirred vigorously until the evolution of gas ceased. Allyl bromide (6.3 g) was added by syringe, and the resultant mixture was stirred at room temperature for 18 hours. The mixture was carefully poured into ice water, and the aqueous mixture was extracted with ethyl acetate (3×). The combined extracts were washed with water and brine (once each), dried (MgSO4), and rotary evaporated to yield 11.1 g of 2,2-diphenyl-4-pentenenitrile, as an oily product.

A mixture of 2,2-diphenyl-4-pentenenitrile (2.33 g), 3.0M ethylmagnesium bromide in ether (10 ml), and benzene (30 ml) was heated at reflux for 3 hours, with stirring. After cooling to room temperature, the crude intermediate was stirred with 1N hydrochloric acid for 3 hours. The hydrolysate was partitioned between water and ethyl acetate (3×). The combined extracts were washed with water and brine, dried (MgSO4), and rotary evaporated to give a crude material which was flash-chromatographed over silica gel. Elution with hexane/ethyl acetate (5:1) yielded 1.0 g of 4,4-diphenyl-6-hepten-3-one, as a colorless oil.

4,4-diphenyl-6-hepten-3-one (144 mg) was dissolved in a mixture of dioxane and water (3:1, 11 ml). A 10% aqueous osmium tetroxide solution (0.5 ml) was added. The resultant solution was stirred at room temperature for 5 min. A solution of sodium periodate (550 mg) in water was then added dropwise. The reaction mixture was allowed to stir for 16 hours. Water was added, and the aqueous mixture was extracted with ethyl acetate (3×). The combined extracts were washed with water (once) and dried (MgSO4). Rotary evaporation of the solution gave a crude product which was purified by preparative thin layer chromatography (PTLC) on silica gel. Development with hexane/ethyl acetate (2:1) produced three bands. The lowest band (Rf 0.66) was scraped off the plate and eluted with methanol to yield 25 mg of 3,3-diphenyl-4-oxo-hexanal.

Fifteen milligrams of 3,3-diphenyl-4-oxo-hexanol (0.043 mmol) was dissolved in DMSO (1 ml). A 10 mg/ml thyroglobulin solution was prepared by dissolving 170 mg of thyroglobulin in 17 ml 0.05M phosphate buffer, pH 9.0. While stirring, the dissolved hapten was added dropwise to the thyroglobulin solution. The hapten vial was rinsed with an additional 0.5 ml DMSO and added dropwise to the solution. The resultant mixture was stirred at room temperature for 1 hour. Five milligrams of sodium cyanoborohydride was added to the mixture, and the solution was stirred at room temperature for 0.5 hours. The pH of the solution was adjusted to 7.5 with 0.1N HCl. An additional 5.0 mg sodium cyanoborohydride was added, and the solution was again stirred for 0.5 hours. This was repeated once more, for a total addition of 15.0 mg sodium cyanoborohydride. This solution was dialyzed against 0.05M phosphate buffer (pH 7.5). The solution was clarified by centrifuging for 10 min at 4000 rpm to produce a solution of 3,3-diphenyl-4-oxo-hexanal, thyroglobulin immunogen.

EXAMPLE 3

5,5-diphenyl-6-oxo-3-octenoic acid, thyroglobulin immunogen

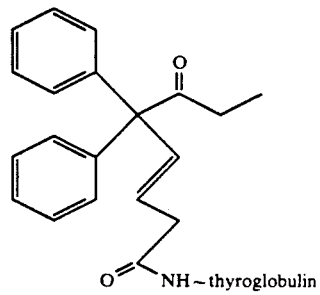

A mixture of 3,3-diphenyl-4-oxo-hexanal (45 mg)[from Example 2], malonic acid (40 mg) and pyridine (1.5 ml) was heated at 80°-90° C. for 18 hours, with stirring. The volatiles were removed in vacuo and the residue was partitioned between water and chloroform (3×). The combined extracts were washed with water and dried (Na2SO4). Rotary evaporation of the solution gave a crude material which was purified by PTLC. Development with hexane/ethyl acetate (2:1) produced two bands. The lower band which was near the origin was scraped off the plate and eluted with methanol. Rotary evaporation of the solution yielded 38 mg of 5,5-diphenyl-6-oxo-3-octenoic acid.

Nineteen milligrams of 5,5-diphenyl-6-oxo-3-octenoic acid (0.062 mmol) was dissolved in p-dioxane (1.0 ml), swirling to dissolve the hapten off the sides of the scintillation vial. The color of the solution was a yellow-brown color. While stirring, isobutylchloroformate (11 μl) and then triethylamine (11 μl) was added to the solution. The solution turned a milky-white color. The solution was allowed to continue stirring at room temperature for 1 hour. A 10 mg/ml thyroglobulin solution was prepared by dissolving 250 mg of thyroglobulin in 25 ml 0.05M phosphate buffer, pH 9.5. The dissolved hapten was added dropwise to the thyroglobulin solution, and the resultant solution was stirred at room temperature for 1 hour. The solution was dialyzed against 0.05M phosphate buffer, pH 7.5. The precipitate disappeared after dialysis to produce a solution of 5,5-diphenyl-6-oxo-3-octenoic acid, thyroglobulin immunogen.

Synthesis of Tracers

EXAMPLE 4

6,6-diphenyl-8-dimethylaminononanoic acid, aminofluorescein amide tracer

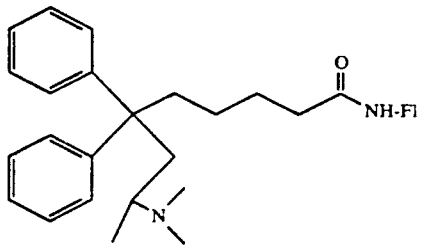

A solution of 4-dimethylamino-2,2-diphenylpentanal (from Example 1)[3.7 g, 13.16 mmol] in benzene (20 ml) was evaporated to dryness on a rotary evaporator to provide a clear oil. After repetition of the azeotropic drying, the aldehyde was pumped down under high vacuum for 30 min. Zinc granules (1.71 g) were added to a 250 ml oven-dried, two-necked flask, equipped with a Freidrich condenser, stir bar and septa. The flask was flame dried under argon (Ar) flow (dry nitrogen). After cooling, the aldehyde in benzene (20 ml) was added, followed by an additional 40 ml of benzene. Distilled ethyl 4-bromocrotonate (5.5 ml, 40 mmol) was added to the stirred suspension, and the reaction mixture was refluxed under Ar, followed by TLC (20% methanol/$CHCl_3$) until the aldehyde could no longer be detected (approximately 45 min). The orange-brown reaction mixture was cooled to room temperature, treated with saturated $NH_4Cl$ (5 ml) and ethyl acetate (100 ml), and vigorously stirred for 10 min. The clear organic layer was decanted from the resulting white aqueous precipitate, and the precipitate was extracted again with ethyl acetate (75 ml). The organic layers were transferred to 250 ml separatory funnel, and the remainder of the aqueous material was drawn off.

The organic extracts were concentrated and diluted with ether (50 ml) to precipitate the inorganic solids. The suspension was diluted with ethyl acetate/ether (2:1, 50 ml), then the solids were removed by filtration through a pad of celite. The filtrate was concentrated to dryness and applied to a column of flash silica gel. Elution with 3.5% methanol in $CHCl_3$ provided 2.30 g of the desired alpha/gamma alcohols. The NMR (200 MHz) of this glassy solid indicated that the ratio of gamma to alpha addition was 84:16, and there was some unreacted 4-bromocrotonate present. The mixture was reapplied to a fresh column as described above to yield 1.77 g of ethyl 8-dimethylamino-6,6-diphenyl-5-hydroxynon-2-enoate.

Triethylamine (2.49 ml, 17.88 mmol) was added to a stirred solution of ethyl 8-dimethylamino-6,6-diphenyl-5-hydroxynon-2-enoate (1.77 g, 4.47 mmol) in $CH_2Cl_2$ (30 ml) at $-30°$ C. ($CCl_4$/acetone/$CO_2$), and the solution was stirred for 5 min. Trifluoromethanesulfonyl chloride (0.38 ml, 4.91 mmol) was then added dropwise. The reaction mixture was stirred 15 min at $-30°$ C., warmed to room temperature over 1 hour, and then stirred at room temperature for 2 hours. The mixture was diluted with $CH_2Cl_2$ (20 ml) and poured into 5% $NaHCO_3$ (20 ml). The layers were separated, and the organic extracts were washed with brine (30 ml). The extracts were dried over $Na_2SO_4$/trace $K_2CO_3$, filtered, and concentrated in vacuo on a rotary evaporator. The oily brown residue was applied to a column as described above, and eluted with 6% methanol in $CHCl_3$ to yield 1.05 g of ethyl 6,6-diphenyl-8-dimethylaminonona-2,4-dienoate, as a clear light brown mobile oil.

1.05 g of ethyl 6,6-diphenyl-8-dimethylaminonona-2,4-dienoate was dissolved in toluene (5 ml) and evaporated to dryness twice. The oil was taken up in 95% ethanol (25 ml) and placed in a Paar shaker bottle with 10% palladium on activated carbon (Pd/C, 190 mg). Paar shaker hydrogenation was conducted at room temperature and 60 psi pressure. After 1 hour, an additional 150 mg of catalyst were added and the hydrogenation reaction continued for 3 hours. TLC indicated complete reaction. The catalyst was removed by filtration, and the filtrate was concentrated to dryness to provide 863 mg of ethyl 6,6-diphenyl-8-dimethylaminononanoate, as a clear light yellow oil.

Ethyl 6,6-diphenyl-8-dimethylaminononanoate (863 mg) was taken up in methanol (7 ml) and treated with 1M KOH in methanol (7.4 ml). The mixture was refluxed under Ar for 2.5 hours, and cooled. The pale yellow solution was concentrated to dryness to provide a clear pale yellow glass. The residue was taken up in $H_2O$ (2 ml) and treated dropwise with 1N HCl to pH 6. This solution was then evaporated to dryness and dissolved in 12 ml of methanol to yield a precipitate which was filtered. This procedure was repeated, using 8 ml of methanol, and the filtrates were evaporated to dryness. A 250 mg portion, dissolved in methanol (12 ml), was purified by PTLC. Development with 30% methanol/$CHCl_3$ produced a major band (Rf range 0.12–0.31), which was scraped off the plate and eluted with methanol. The methanolic extracts were evaporated, and the residue was coevaporated twice with toluene (3 ml) to yield 167 mg of 6,6-diphenyl-8-dimethylaminononanoic acid, as a clear oil.

Isobutylchloroformate (5.8 μl, 0.045 mmol) was added to a cold solution (0° C.) of 6,6-diphenyl-8-dimethylaminononanoic acid (15.6 mg, 0.044 mmol) in dry 1,4-dioxane (0.24 ml) and freshly distilled THF (0.11 ml), and the resultant mixture was stirred at 0° C. for 130 min. The solution turned opaque. Fluorescein amine isomer I in N-methylpyrrolidinone (0.16 ml) was added, and the mixture was warmed to room temperature. After 40 hours of stirring in diffuse light, the reaction mixture was treated with 3 drops of a saturated sodium carbonate solution and stirred 5 min. The mixture was then carefully neutralized with 10% HCl (7 drops) and finally with 0.05M Phosphate buffer, pH 7.5. The suspension was made soluble with 3.5 ml of methanol and concentrated to 2.5–3.0 ml in vacuo. The product was applied to preparative TLC plates and developed twice with 30% methanol in chloroform. The fluorescent band at Rf range 0.26–0.35 was removed and eluted from the gel with methanol. After concentration, the tracer was applied to a single reversed phase silica gel plate and developed once with 50% acetonitrile in 10 mM ammonium acetate. The desired band was removed from the plate, eluted with methanol and concentrated to provide 10.9 mg of pure 6,6-diphenyl-8-dimethylaminononanoic acid, aminofluorescein amide tracer.

EXAMPLE 5

6-dimethylamino-4,4-diphenyl-heptanoic acid, aminofluorescein amide tracer

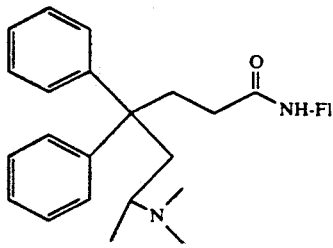

The phosphonate anion was generated by dropwise addition of a solution of trimethylphosphonoacetate (182 mg) in 1,2-dimethylethane (DME, 1 ml) to a slurry of 80% sodium hydride (24 mg, prewashed with hexane) in DME (3 ml). After stirring at room temperature for 30 min, a solution of 4-dimethylamino-2,2-diphenyl-pentanal (281 mg), as prepared in Example 1, in DME (1 ml) was added slowly. The mixture was allowed to stir for 24 hours. Water was added, and the aqueous mixture was extracted with ethyl acetate (3×). The combined extracts were washed with water and brine (once each), and dried (MgSO4). Rotary evaporation of the solution gave a crude product which was flash-chromatographed over silica gel. Elution with chloroform/methanol (20:1) yielded 93 mg of methyl 6-dimethylamino-4,4-diphenyl-2-heptenoate.

A mixture of methyl 6-dimethylamino-4,4-diphenyl-2-heptenoate (60 mg), 10% Pd/C (10 mg), and methanol was hydrogenated at room temperature for 18 hours. The mixture was filtered through a short pad of celite, and the filtrate was rotary evaporated to give methyl 6-dimethylamino-4,4-diphenyl-heptanoate, as a crude material which was then dried in vacuo.

A mixture of methyl 6-dimethylamino-4,4-diphenyl-heptanoate (obtained above), potassium carbonate (500 mg), methanol (5 ml) and water (1 ml) was stirred at room temperature for 24 hours. The reaction mixture was diluted with water, acidified with 1N HCl to pH 1, and extracted with chloroform (3×). The combined extracts were washed with water and brine (once each). After drying over magnesium sulfate, the solution was rotary evaporated to yield 40 mg of 6-dimethylamino-4,4-diphenyl-heptanoic acid.

A mixture of 6-dimethylamino-4,4-diphenyl-heptanoic acid (3.25 mg), dicyclohexyl carbodiimide (4.1 mg), N-hydroxysuccinic hydride (1.3 mg) and pyridine (0.2 ml) was stirred at room temperature for 1 hour. Fluorescein amine isomer II (3.47 mg) was added, and the mixture was allowed to stir for 18 hours. The crude products were applied onto two preparative TLC plates. Development with chloroform/methanol (3:1) gave four major bands. The desired band was scraped off the plates and eluted with methanol to yield pure 6-dimethylamino-4,4-diphenyl-heptanoic acid, aminofluorescein amide tracer.

EXAMPLE 6

3,3-diphenyl-4-oxo-hexanal-1-(O-carboxymethyl)oxime, aminofluorescein amide tracer

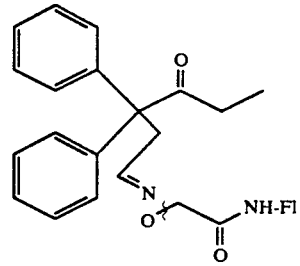

A mixture of 3,3-diphenyl-4-oxo-hexanal (10 mg) [from Example 2], carboxymethoxylamine hemihydrochloride (14 mg), sodium bicarbonate (5 mg) and absolute ethanol was stirred at room temperature for 16 hours. Water was added, and the aqueous mixture (pH 4) was extracted with ethyl acetate (3×). The combined extracts were washed with water and dried (MgSO4). Rotary evaporation of the solution gave a crude product which was purified by PTLC. Development with chloroform/methanol (5:1) produced three bands. The middle band (Rf 0.3) was scraped off the plate and eluted with methanol. Rotary evaporation of the eluent yielded 6.7 mg of 3,3-diphenyl-4-oxo-hexanal-1-(O-carboxymethyl)oxime, as an oily residue which was further dried in vacuo.

Dicyclohexyl carbodiimide (4.5 mg) was added to a stirred solution of 3,3-diphenyl-4-oxo-hexanal-1-(O-carboxymethyl)oxime (3.4 mg) in pyridine (0.2 ml), at room temperature. N-hydroxy succinimide (2.0 mg) was added. Stirring was continued for 2 hours, then fluorescein amine isomer I was added. The mixture was allowed to stir for 16 hours. The crude products were applied onto a preparative TLC plate. Development with chloroform/methanol (3:1) gave the individual tracer bands which were eluted with methanol to yield pure 3,3-diphenyl-4-oxo-hexanal-1-(O-carboxymethyl)oxime, aminofluorescein amide tracer.

EXAMPLE 7

4-oxo-3,3-diphenylhexanoic acid, aminomethylfluorescein amide tracer

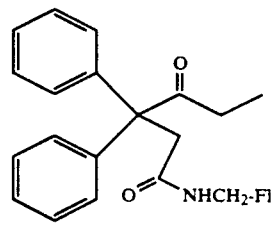

A solution of 4,4-diphenylhept-6-ene-3-one (134.2 mg, 0.51 mmol) in benzene (1 ml) was added to a vigorously stirred suspension of potassium permanganate (322 mg, 2.03 mmol) and tricaprylmethylammonium chloride (10 mg) in benzene/water (1:1, 2 ml). After 14 hours of vigorous stirring, the mixture was diluted with benzene (20 ml), and treated with excess sodium hydrosulfite and 1N HCl added to destroy unreacted KMnO4. The mixture was transferred to a separatory funnel, and the aqueous layer was drawn off. The organic extract was washed with water and dried (MgSO₄). Filtration and concentration in vacuo provided 124 mg of 4-oxo-3,3-diphenylhexanoic acid, as a viscous pale yellow oil.

Anhydrous triethylamine (5.0 μl, 0.035 mmol) was added to a solution of 4-oxo-3,3-diphenylhexanoic acid (8.8 mg, 0.031 mmol) in anhydrous dioxane (0.3 ml). While stirring, isobutylchloroformate (4.2 μl, 0.033 mmol) was added, and the mixture stirred at room temperature for 30 min. The mixed carbonate thus prepared was added by syringe to a stirred solution of aminomethylfluorescein hydrochloride (11.1 mg, 0.028 mmol) and triethylamine (8.5 μl) in anhydrous N,N-dimethylformamide (DMF, 0.1 ml). The mixture was stirred at room temperature in the dark for 18 hours, evaporated to dryness and applied to a PTLC plate. The plate was developed twice with 5% methanol in chloroform to produce a band in the range of Rf 0.34–0.39. This band was scraped off the plate, eluted and repurified on another plate to yield 0.2 mg of pure 4-oxo-3,3-diphenylhexanoic acid, aminomethylfluorescein amide tracer.

EXAMPLE 8

6-oxo-5,5-diphenyloctanoic acid, aminofluorescein amide tracer

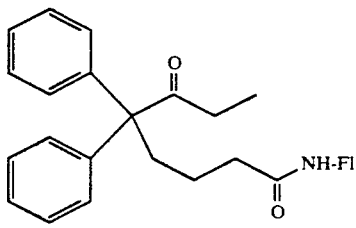

A solution of diphenylacetonitrile (966 mg, 5.0 mmol) in dry THF (10 ml) was added dropwise to a stirred suspension of hexane-washed NaH in THF (10 ml) at 0° C. When gas evolution ceased, the mixture was warmed to room temperature, and 5-bromo-1-pentene (0.71 ml, 6.0 mmol) was added by syringe. The mixture was warmed to reflux for 16 hours, cooled, treated with 0.5 ml of 1N HCl, and evaporated to dryness. The residue was taken up in 30 ml ethyl acetate, washed with brine and dried (MgSO₄). Filtration, followed by evaporation, yielded 1.26 g of 1,1-diphenyl-5-hexenenitrile.

Diisobutylaluminum hydride (DIBAH, 2.5 ml of a 1.5M solution in toluene, 3.75 mmol) was added at −78° C. to a solution of 1,1-diphenyl-5-hexenenitrile (911 mg, 3.4 mmol) in dry THF (6 ml). The mixture was allowed to slowly come to room temperature overnight. The mixture was cast into 100 ml of cracked ice, 30 ml of 6N H2SO4, and the aqueous mixture was stirred for 15 min. The mixture was extracted (3×) with ether (20 ml each), and the ethereal layers were combined, washed with brine and dried (MgSO₄). Evaporation of the solvents provided 768 mg of 6,6-diphenylhept-6-enal.

Seven hundred sixty-eight milligrams of 6,6-diphenylhept-6-enal were dissolved in dry THF (10 ml), cooled to 0° C., and treated with 1.5 ml of a 3.0M solution of ethylmagnesium bromide in ether. After stirring 1 hour at room temperature, the mixture was quenched with saturated ammonium chloride solution and diluted with ether. The ethereal extracts were washed with brine, and evaporated to dryness. The residue was applied to column of SiO2, and eluted with a gradient of 5 to 25% ether in hexane to provide 170 mg of pure 4,4-diphenylnon-8-en-3-ol.

One hundred seventy milligrams of 4,4-diphenylnon-8-en-3-ol was dissolved in acetone (10 ml), and then treated with 2.7M chromic acid solution (0.04 ml). After 10 min, the excess oxidant was destroyed with isopropanol, and the mixture was diluted with ether (20 ml). Filtration through a pad of celite and concentration yielded 133 mg of 4,4-diphenylnon-8-en-3-one, as an amorphous white solid.

Oxidation of 4,4-diphenylnon-8-en-3-one, following the same procedure as described in Example 7, provided 54 mg of 6-oxo-5,5-diphenyloctanoic acid.

While stirring, bis(2-oxo-3-oxazolidinyl)-phosphinic chloride (BOP-Cl, 8.4 mg, 0.033 mmol) was added at room temperature to a solution of 6-oxo-5,5-diphenyloctanoic acid (10.4 mg, 0.033 mmol), fluorescein amine isomer 1 (11.4 mg, 0.033 mmol) and triethylamine (20 μl, 0.069 mmol). The reaction mixture was stirred at room temperature for 72 hours, and then the solvents were removed in vacuo. The residue was taken up in a minimal amount of methanol, applied to a plate and developed three times with 10% methanol in chloroform. The band at Rf range 0.75–0.89 was removed and eluted from the gel with methanol. The material was similarly chromatographed on a plate with two developments of 15% methanol in chloroform to provide 0.6 mg of pure 6-oxo-5,5-diphenyloctanoic acid, aminofluorescein amide tracer.

EXAMPLE 9

N-(2-aminoethyl)-8-dimethylamino-6,6-diphenyl-5-hydroxynonylamine, DTAF tracer

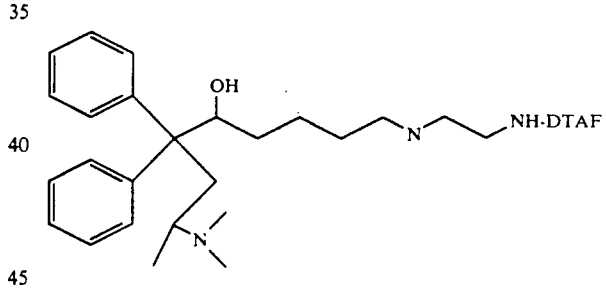

Ethylenediamine was added to a solution of 2-dimethylamino-4,4-diphenyl-5-oxononanal (12 mg), as prepared in Example 1, in methanol (0.5 ml). After the mixture was stirred at room temperature, sodium cyanoborohydride (10 mg) was added. The mixture was stirred at room temperature for 18 hours, water was added, and the aqueous mixture was extracted with chloroform. The combined extracts were washed with brine and dried (MgSO₄). Rotary evaporation gave a crude product which was further dried in vacuo to yield 4 mg of N-(2-aminoethyl)-8-dimethylamino-6,6-diphenyl-5-hydroxynonylamine.

A mixture of N-(2-aminoethyl)-8-dimethylamino-6,6-diphenyl-5-hydroxynonylamine (4 mg), DTAF isomer 1 (3 mg), triethylamine (1 drop) and methanol (0.2 ml) was stirred at room temperature for 18 hours. The mixture was applied to a preparative TLC plate. Development with chloroform/methanol (3:1) gave four bands. The desired bands were scraped off the plate and eluted with methanol to yield pure N-(2-aminoethyl)-8-dimethylamino-6,6-diphenyl-5-hydroxynonylamine, DTAF tracer.

Methadone Fluorescence Polarization Immunoassays

As described previously, the reagents for the FPIA of the present invention comprise tracers and antibodies raised against immunogens of the present invention, specific for methadone. In addition, conventionally used assay solutions including a dilution buffer, and methadone calibrators and controls are prepared.

The preferred procedure was designed to be used in conjunction with the automated TDx or ADx system; however, manual assays can also be performed. In both procedures, the test sample can be mixed with a pre-treatment solution in dilution buffer before a background reading is taken. The tracer is then added to the test solution, followed by the addition of the antibody. After incubation, a fluorescence polarization reading is taken.

In the automated assays, the fluorescence polarization value of each calibrator, control or test sample is determined and printed on the output tape of the TDx or ADx instrument. The instrument also generates a standard curve by plotting the polarization of each calibrator versus its concentration, using a nonlinear regression analysis. The concentration of each control or sample is read off the stored calibration curve and printed on the output tape.

The following reagents were used in the preferred automated methadone assay:

1) the pre-treatment solution comprising 4 mg/ml RBP in 0.1M Tris buffer, pH 7.5, containing 0.01% bovine gamma-globulin and 0.1% sodium azide;
2) the tracer diluted in 5% cholic acid in TDx buffer (0.1M phosphate buffer, pH 7.5, containing 0.01% bovine gamma-globulin and 0.1% sodium azide);
3) the antibody, comprising sheep antisera raised against a methadone immunogen, diluted in 0.1M citrate, pH 7.5, with 2% ethylene glycol and 0.1% sodium azide;
4) a wash solution comprising TDx buffer;
5) a diluent buffer comprising TDx buffer;
6) calibrators comprising pooled normal human urine preserved with 0.1% sodium azide containing 0.00, 0.15, 0.25, 0.50, 1.00 and 4.00 µg/ml methadone; and
7) controls comprising pooled normal human urine preserved with 0.1% sodium azide containing 0.30, 0.75 and 2.00 µg/ml methadone.

All polarized fluorescent measurements were made using the TDx instrument which performed the assay in accordance with the following protocol:

1) 25 µl of standard or unknown test sample were delivered into a predilute well, and a sufficient volume of diluent buffer was added to raise the volume to 500 µl;
2) a portion of sample from the predilute well and 12.5 µl of pre-treatment solution were pipetted into a cuvette, and a background intensity reading was taken;
3) 25 µl each of tracer and antibody, and the remaining portion of sample were added to the cuvette, and a sufficient volume of diluent buffer was added to raise the volume to 2.0 ml;
4) the reaction mixture was incubated;
5) the fluorescence polarization due to tracer binding to the antibody was obtained by subtracting the polarized fluorescence intensities of the background from the final polarized fluorescence intensities of the mixture; and
6) the polarization value for the unknown test sample was compared to a standard curve prepared using calibrators of known methadone content.

EXAMPLE 10

FPIA

Data obtained from an immunoassay according to the present invention are summarized herein. The binding of tracer to antibody and the displacement of the tracer by the methadone present in the sample are summarized in Table 1 below. Various combinations of antibodies developed in response to immunogens and tracers, as described in the Examples above, were tested. In each combination where the tracer bound to the antibody, the net millipolarization value was at least 150 millipolarization units, the span was at least 80 millipolarization units, and the intensity ratio varied between ten and twenty times that of background noise. The combination of the antibody produced by the immunogen of Example 2 and the tracer of Example 4 provided unexpected results insofar as the tracer showed good binding to the antibody and good displacement by methadone, with a hapten of the immunogen which is structurally different than the analyte-analog of the tracer.

TABLE 1

| Immunogen | Tracer | Net Polarization* | Span* | Intensity** |
|---|---|---|---|---|
| Example 1 | Example 4 | 218 | 175 | 14 |
|  | Example 8 | *** | *** | 15 |
| Example 2 | Example 4 | 192 | 132 | 17 |
|  | Example 8 | 224 | 127 | 11 |
| Example 3 | Example 4 | *** | *** | 20 |
|  | Example 8 | 251 | 89 | 12 |

*in millipolarization units
**expressed as a ratio of net intensity to background noise
***binding of tracer to antibody was too low to use for span testing The methadone FPIA system of the present invention is specific for methadone. The cross-reactivity of a variety of structurally similar drugs was tested, as summarized in Table 2 below. Compounds were assayed by adding a known quantity of the test compound to drug-free normal human urine and assaying the test samples on the TDx instrument. The compounds were tested at a concentration of 100 µg/ml. The antisera, produced in response to the immunogens of the present invention, are highly specific to methadone which in combination with the tracers of the present invention provide a sensitive FPIA for methadone.

TABLE 2

| | FPIA Specificity | | | |
|---|---|---|---|---|
| | Immunogen | | | |
| | Example 1 | Example 2 | | Example 3 |
| Test Compound | Tracer 4 | Tracer 4 | Tracer 8 | Tracer 8 |
| Amitriptyline | 0.16 | 0.36 | 0.09 | 0.00 |
| Trans-amitriptyline | 0.07 | 0.05 | 0.01 | 0.00 |
| Trimipramine | 0.15 | 0.37 | 0.10 | 0.00 |
| Clomipramine | 0.14 | 0.28 | 0.08 | 0.00 |
| Promethazine | 0.22 | 0.23 | 0.07 | 0.00 |
| Promazine | 0.19 | 0.21 | 0.08 | 0.00 |
| Triflupromazine | 0.13 | 0.02 | 0.01 | 0.00 |
| Chlorpromazine | 0.20 | 0.14 | 0.04 | 0.00 |
| Dextropropoxyphene | 0.03 | 1.05 | 1.04 | 0.00 |
| Diphenhydramine | 0.13 | >4.00 | >4.00 | 0.00 |

In addition, the methadone FPIA of the present invention was also tested for cross reactivity with the major urinary metabolites of methadone. The metabolites were assayed at a concentration of 100 µg/ml.

Neither the primary metabolite, 2-ethylidene-1,5-dimethyl-3,3-diphenylpyrrolidine (EDDP), nor the secondary metabolite, 2-ethyl-5-methyl-3,3-diphenylpyrroline (EMDP) showed cross reactivities higher than the sensitivity of the assay, 0.10 μg/ml, as summarized in Table 3.

TABLE 3

| | FPIA Specificity |
|---|---|
| Test Compound | Immunogen 1, Tracer 4* |
| EDDP | <0.10 |
| EMDP | <0.10 |

*Concentration in μg/ml

Optionally, promethazine can be utilized in the assay system. The addition of promethazine to the assay minimizes the effect of any slight interference due to structurally similar compounds present in high concentrations. The concentration of promethazine can range from about 1 to 20 μg/ml, preferably from about 8 to 12 μg/ml, with a concentration of about 10 μg/ml being most preferred.

An experiment was conducted wherein 10 μg/ml promethazine was added to the sample pre-treatment reagent used. Two percent sodium ascorbate was also added to the pre-treatment reagent. The combination of the antibody produced by the immunogen of Example 1 and the tracer of Example 4 was utilized. As summarized in Table 4, the addition of promethazine still provided an assay with an acceptable net millipolarization value, span and intensity.

TABLE 4

| | Net Polarization* | Span* | Intensity** |
|---|---|---|---|
| Without promethazine | 218 | 175 | 14 |
| With promethazine | 162 | 118 | 16 |

*in millipolarization units
**expressed as a ratio of net intensity to background noise In addition, the cross-reactivity of a variety of structurally similar drugs was tested. The compounds were tested at a concentration of 100 μg/ml. As summarized in Table 5, the addition of promethazine into the pre-treatment reagent provided an assay wherein the signal due to the cross-reactivities of the structurally-related compounds was reduced to levels below the sensitivity of the assay, 0.10 μg/ml. The methadone FPIA specifically measures the quantity of methadone in a sample, and the assay has minimal cross-reactivity to structurally similar compounds.

TABLE 5

| | FPIA Specificity | |
|---|---|---|
| Test Compound | Without promethazine | With promethazine |
| Amitriptyline | 0.16 | 0.07 |
| Trans-amitriptyline | 0.07 | 0.03 |
| Trimipramine | 0.15 | 0.06 |
| Clomipramine | 0.14 | 0.07 |
| Promethazine | 0.22 | 0.05 |
| Promazine | 0.19 | 0.07 |
| Triflupromazine | 0.13 | 0.04 |
| Chlorpromazine | 0.20 | 0.08 |
| Dextropropoxyphene | 0.03 | 0.00 |
| Diphenhydramine | 0.13 | 0.05 |

It will be appreciated by one skilled in the art that many of the concepts of the present invention are equally applicable to other types of binding assays. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. An immunogen useful in eliciting antibodies for determining the presence or amount of methadone in a test sample, comprising the structure:

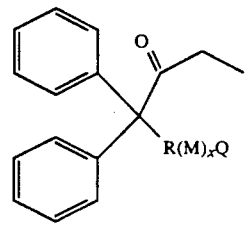

wherein
R is a member of the group consisting of —CH₂CH₂—, —CH=CH—CH₂—, and —CH₂CH=N—O—CH₂—;
x is 0 or 1;
M is C=O; and
Q is an immunogenic carrier.

2. The immunogen of claim 1 wherein
R is —CH₂CH₂—;
x is 0; and
Q is thyroglobulin.

3. The immunogen of claim 1 wherein
R is —CH=CH—CH₂—;
x is 1;
M is —C=O; and
Q is thyroglobulin.

4. The immunogen of claim 1 wherein
R is —CH₂CH=N—O—CH₂—;
x is 1;
M is —C=O; and
Q is thyroglobulin.

5. An immunogen useful in eliciting antibodies for determining the presence or amount of methadone in a test sample, comprising the structure:

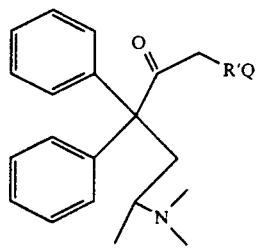

wherein
R' is a spacer group consisting of from 2 to 10 carbon atoms arranged in a straight or branched, saturated or unsaturated, chain; and
Q is an immunogenic carrier.

6. The immunogen of claim 5 wherein
R' is (—CH₂—)₄; and
Q is thyroglobulin.

* * * * *